US006574301B1

(12) United States Patent
Jansen

(10) Patent No.: US 6,574,301 B1
(45) Date of Patent: Jun. 3, 2003

(54) CT DATA ACQUISITION SYSTEM TRIGGER JITTER FILTER

(75) Inventor: Michael Shane Jansen, Wauwatosa, WI (US)

(73) Assignee: GE Medical Systems Global Technology Company, LLC, Waukesha, WI (US)

( * ) Notice: Subject to any disclaimer, the term of this patent is extended or adjusted under 35 U.S.C. 154(b) by 0 days.

(21) Appl. No.: 10/073,786

(22) Filed: Feb. 11, 2002

(51) Int. Cl.$^7$ ................................................. A61B 6/03
(52) U.S. Cl. ............................ 378/20; 378/15; 378/901
(58) Field of Search ................................. 378/4, 15, 20, 378/901

(56) References Cited

U.S. PATENT DOCUMENTS

| | | | |
|---|---|---|---|
| 5,272,627 A | 12/1993 | Maschhoff et al. | |
| 5,740,224 A | 4/1998 | Muller et al. | |
| 5,821,541 A | 10/1998 | Tumer | |
| 6,028,412 A | * 2/2000 | Shine et al. | ................. 318/696 |
| 6,298,459 B1 | * 10/2001 | Tsukamoto | ................. 714/746 |

* cited by examiner

Primary Examiner—David V. Bruce
(74) Attorney, Agent, or Firm—Quarles & Brady, LLP; Carl Horton

(57) ABSTRACT

A method and apparatus for reducing trigger jitter from a CT system position encoder including the steps, for each trigger pair in the encoder signal, identifying the integer portion of average period corresponding to N preceding trigger pairs, identifying a modulus-N residual corresponding to the N preceding trigger pairs as a lag value, adding the lag value to a lag count, determining when the lag count exceeds N and, where the lag count exceeds N, incrementing the integer portion by one, identifying a modulus-N residual corresponding to the lag count, setting the lag count equal to the residual corresponding to the lag count and generating a final binary trigger signal corresponding to the integer portion.

19 Claims, 3 Drawing Sheets

CT DATA ACQUISITION SYSTEM TRIGGER JITTER FILTER

STATEMENT REGARDING FEDERALLY SPONSORED RESEARCH

Not applicable.

CROSS-REFERENCE TO RELATED APPLICATIONS

Not applicable.

BACKGROUND OF THE INVENTION

The present invention relates to computerized tomography and more particularly to a method and apparatus for minimizing the effects of gantry jitter on image quality.

In computerized tomography (CT) a patient is positioned on a support table with a portion of a patient to be imaged (hereinafter "a region of interest") disposed within an imaging area, an X-ray photon source and a detector array are mounted to an annular gantry on opposite sides of the imaging area and the gantry, including the detector and the source, are rotated about the imaging area so that photon rays from the source are directed through the region of interest toward a detector opposite the source. In addition to the rotational motion, the support table may be translated through the imaging area so that the rays sweep a helical path through the region of interest. Attenuated rays are detected by the detector, the amount of attenuation indicative of the make up (e.g. bone, flesh, air pocket, etc.) of the region of interest through which the rays traverse.

The attenuation data is processed and grouped into separate "views" about the patient where each view corresponds to a specific gantry orientation and hence a specific source position or angle with respect to the imaging area. Thereafter, the views are back-projected according to a reconstruction algorithm to generate an image of the region of interest. Generally, the "back projection" is performed in software but, as the name implies, is akin to physically projecting views from many different angles within an image plane through the image plane, the view rays passing through the same image voxels being combined in some manner to have a combined effect on the voxel in the resulting image.

In order to group the attenuation data into separate views, ideally, the 360 degrees of gantry rotation are equally divided into view angle ranges (hereinafter "view ranges") corresponding to the required number of views and then the data collected within each separate view range is binned together to form a corresponding view. For instance, where 984 separate views are required to construct an image, the 360 degree range is divided into 984 separate view ranges of approximately 0.3659 degrees each. Thereafter, data collected within each separate view range during a single source rotation is stored as a separate view. In operation, during data acquisition, the system tracks source orientation and, when the source transitions from a first position within a first view range to a second position within a second view range, the system generates a trigger signal causing the system to begin binning the data in a new view corresponding to the second view range.

One useful method for identifying source orientation and determining if the source angle is within a specific angle range has been to provide a ring encoder linked to the gantry that senses gantry position and generates source location trigger signals. For instance, an exemplary encoder may be capable of differentiating 106,496 separate and equispaced source orientations (i.e., the encoder has a 106,496 position resolution). Where 984 separate views are required, the 106,496 encoder positions are divided into 984 separate position ranges corresponding to the 984 views. Hereinafter the ratio of encoder resolution to required views is referred to as the encoder-view ratio.

In the example above, where the gantry rotates at one rotation per second, the encoder generates a signal having a frequency of precisely 106,496 Hz and data corresponding to 984 views is collected for every gantry rotation. Where gantry rotation frequency is increased, the encoder frequency and view frequency increase proportionally. For instance, where rotation frequency is 2 Hz, the encoder and view frequencies are doubled to 212,992 Hz and 1968 Hz, respectively. Hereinafter the encoder and view acquisition frequencies will be referred to generally as encoder frequency and view frequency, respectively.

Encoder type systems like the system described above have two important shortcomings. First, often the encoder frequency does not divide evenly by the view frequency. For instance, in the example above, the encoder-view frequency ratio is 108.23 (i.e., 106,496 Hz/984 Hz) and therefore the encoder positions cannot be precisely and directly converted into view ranges.

Second, as well known in the CT industry, while attempts have been made to manufacture robust and precise encoders, even high quality encoders tend to jitter (i.e., vibrate) during gantry rotation so that the instantaneous encoder frequency may vary appreciably. For instance, in one CT system the rotating portion of the gantry includes a ring having externally extending teeth and the encoder includes a relatively smaller gear having teeth that mate with the gantry teeth so that the encoder gear spins as the gantry rotates. In an exemplary case the encoder gear rotates at 13 times the gantry rotational frequency and includes 300 teeth. In this case, where the gantry rotation frequency is 1 Hz, the frequency of the encoder signal will often include 13 and 300 Hz noise components.

While not discussed here in detail, it should be noted that the CT imaging environment is often very noisy and therefore there are many other noise sources that pollute the encoder trigger signal so that the trigger signal sequence that is generated often does not precisely reflect the gantry and source position. As with most mechanical systems, the encoder accuracy problems are exacerbated as the encoder components wear over time.

While jitter and encoder-view ratio related frequency inaccuracies may be acceptable in certain applications, in many applications such variations cause image artifacts that appreciably reduce the diagnostic value of resulting images. For instance, where long CINE scans of several minutes are performed, in order to align views from consecutive gantry rotations, the scans require that the first trigger in every rotation occur within 10% of the first trigger in the first scan rotation. This 10% registration requirement requires that the system have minimal trigger signal drift. For instance, if a system were to lose 0.99 triggers every rotation, after only two rotations the drift would be too great for the 10% registration requirement.

To account for fractional encoder-view ratios, many systems feed the encoder signals to a phase locked loop (PLL) circuit. PLLs are well known in the art and therefore will not be explained here in detail. It should suffice to say, in this regard, that a PLL circuit typically receives the encoder signal and generates an output trigger signal every N encoder signals where N is the encoder-view ratio. For instance, in the present example, where the encoder-view ratio is 108.23 (i.e., 106,496/984), the PLL trigger signal is generated approximately every 108.23 encoder signals.

Unfortunately, while the PLL reduces the affects of system noise somewhat, the encoder noise is at least in part reflected in the PLL output trigger signal. For example, where the encoder signal has an instantaneous frequency range of between plus and minus 10% of the ideal encoder frequency (i.e., the encoder frequency that would precisely correspond to gantry position), the PLL trigger signal frequency may have a range of plus or minus 5% of the ideal view frequency. Five percent variance in the frequency spectrum is too great for many applications.

SUMMARY OF THE INVENTION

It has been recognized that the mass of a gantry and components attached thereto is typically large and therefore, during gantry rotation, the gantry and attached components typically maintain their rotational frequency over small rotational ranges despite system noise and instantaneous encoder frequency changes. For this reason recent gantry rotational frequency history can be used to relatively precisely identify trigger times corresponding to different view ranges.

To this end, the present invention includes a filter apparatus that receives the PLL trigger signals and identifies a moving average of the periods corresponding to separate view ranges during data acquisition. Thereafter, the filter apparatus generates a filtered trigger signal that occurs at the average of the most recent view range periods. The filter, in effect, substantially eliminates the effects of jitter from the trigger signals so that the resulting trigger signal more closely mirrors the gantry and source position. For instance, in a typical case, the filtered trigger signal frequency is plus or minus 1% of the actual instantaneous gantry frequency and therefore the trigger signals are more precisely aligned with the gantry position.

In addition, the inventive apparatus retains a running filter error and uses the running error to compensate for drift that the filter could introduce into the trigger signals. To this end, in at least some embodiments, where the moving average period is determined over N trigger cycles, the modulus-N values for consecutive cycles are summed until the modulus-N sum, referred to herein as a lag count, exceeds N. When the lag count exceeds N for any cycle, the integer portion of the moving average is incremented by one to eliminate the effects of drift. In addition, when the lag count exceeds N for any cycle, a modulus-N value for the lag count is determined and the lag count is reset to the modulus-N value.

Consistent with the above, the present invention includes a method for use with a CT system including a gantry mounted position encoder that provides a digital encoder position signal including signal pulses that indicate gantry positions, the system including a phase locked loop (PLL) that receives the position signal and generates an intermediate trigger signal every X/Y position signals, each two consecutive intermediate trigger signals comprising a trigger pair, the method comprising the steps of beginning with the first trigger pair and working toward the last trigger pair in the intermediate signal, for each trigger pair: identifying the average period corresponding to N preceding trigger pairs; and generating a final trigger signal as a function of the average period.

In at least some embodiments the step of identifying includes the steps of identifying the integer portion of the average period, identifying drift in the integer portion, determining when the drift exceeds a threshold value and modifying the integer portion to compensate for the drift when the drift exceeds the threshold value. In addition, the step of identify drift may include the steps of identifying a modulus-N residual corresponding to the N preceding trigger pairs as a lag value and adding the lag value to a lag count.

The step of determining when drift exceeds a threshold value may include the steps of determining when the lag count exceeds N. Moreover, the step of modifying the integer portion may include, when the lag count exceeds N, incrementing the integer portion by one. Here, the method may further include the step of, when the lag count exceeds N, identifying a modulus-N residual corresponding to the lag count and setting the lag count equal to the residual corresponding to the lag count. N may include the N immediately preceding pulse pairs. N, in many embodiments, corresponds to a fraction of a complete gantry rotation. Typically N corresponds to 3 to 50 percent of a complete gantry rotation.

Where the trigger signal is a binary signal including a high time followed by a low time, in at least some embodiments the step of generating the final trigger signal further includes dividing the integer portion by two to generate a half period, rounding the half period up and down to generate ceiling and floor periods, respectively, setting a one of the low and high times equal to one of the floor and ceiling periods' and setting the other of the low and high times equal to the other of the floor and ceiling periods. Here, the steps of setting the low and high times further may include setting the high time equal to the floor period and setting the low time equal to the ceiling period.

The invention also includes a method for use with a CT system including a gantry mounted position encoder that provides a digital encoder position signal including signal pulses that indicate gantry positions, the system including a phase locked loop (PLL) that receives the position signal and generates an intermediate trigger signal every X/Y position signals, each two consecutive intermediate trigger signals comprising a trigger pair, the method comprising the steps of, beginning with the first trigger pair and working toward the last trigger pair in the intermediate signal, for each trigger pair: identifying the integer portion of an average period corresponding to N preceding trigger pairs, identifying a modulus-N residual corresponding to the N preceding trigger pairs as a lag value, adding the lag value to a lag count, determining when the lag count exceeds N and, where the lag count exceeds N: (i) incrementing the integer portion by one, (ii) identifying a modulus-N residual corresponding to the lag count, (iii) setting the lag count equal to the residual corresponding to the lag count and generating a final binary trigger signal including a high time followed by a low time, the step of generating including, dividing the integer portion by two to generate a half period, rounding the half period up and down to generate ceiling and floor periods, respectively, setting one of the low and high times equal to one of the floor and ceiling periods and setting the other of the low and high times equal to the other of the floor and ceiling periods.

Moreover, the invention includes an apparatus for use with a CT system including a gantry mounted position encoder that provides a digital encoder position signal including signal pulses that indicate gantry positions, the system including a phase locked loop (PLL) that receives the position signal and generates an intermediate trigger signal every X/Y position signals, each two consecutive intermediate trigger signals comprising a trigger pair, the apparatus comprising a program running a pulse sequencing program to perform the steps of, beginning with the first trigger pair and working toward the last trigger pair in the intermediate signal, for each trigger pair: identifying an average period corresponding to N preceding trigger pairs and generating a final trigger signal as a function of the average period.

In some embodiments the program causes the processor to perform the step of generating by performing the steps of, identifying the integer portion of the average period, identifying a modulus-N residual corresponding to the N preceding trigger pairs as a lag value, adding the lag value to a lag count, determining when the lag count exceeds N and, where the lag count exceeds N: (i) incrementing the integer portion by one, (ii) identifying a modulus-N residual corresponding to the lag count, (iii) setting the lag count equal to the residual corresponding to the lag count and generating a final binary trigger signal corresponding to the integer portion.

More specifically, where the final trigger signal includes a high time followed by a low time, the program may cause the processor to perform the step of generating by dividing the integer portion by two to generate a half period, rounding the half period up and down to generate ceiling and floor periods, respectively, setting one of the low and high times equal to one of the floor and ceiling periods and setting the other of the low and high times equal to the other of the floor and ceiling periods.

The program may also cause the processor to perform the steps of setting the low and high times by setting the high time equal to the floor period and setting the low time equal to the ceiling period.

These and other objects, advantages and aspects of the invention will become apparent from the following description. In the description, reference is made to the accompanying drawings which form a part hereof, and in which there is shown a preferred embodiment of the invention. Such embodiment does not necessarily represent the full scope of the invention and reference is made therefore, to the claims herein for interpreting the scope of the invention.

DESCRIPTION OF THE PREFERRED EMBODIMENT

A. Hardware

Figure 1:
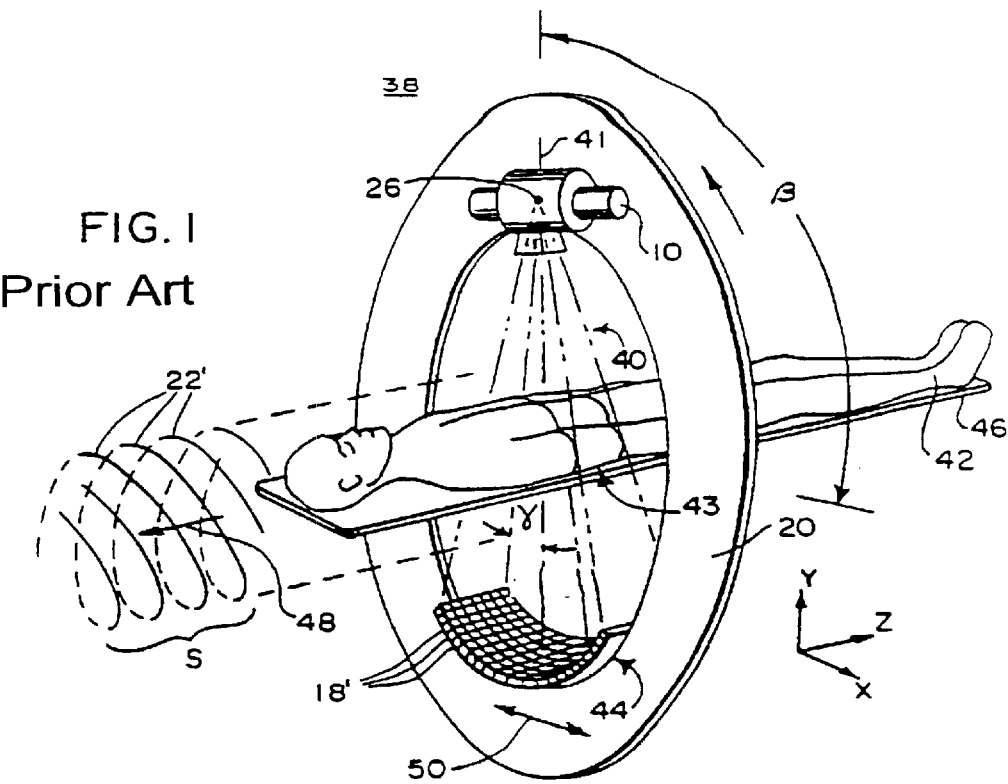
FIG. 1 is a perspective view of a CT apparatus used to practice the present invention which includes a detector array having rows and columns of detector elements and fan beam source.

Referring now to FIG. 1, a CT scanner for use with the present invention includes a gantry 20 having an opening (i.e., defining an imaging area) supporting an x-ray source 10 oriented to project a fan beam 40 of x-rays along the beam axis 41 through a patient 42 to a supported and opposed detector array 44. The gantry 20 rotates to swing the beam axis within a gantry plane 38 defining the x-y plane of a Cartesian coordinate system. Rotation of the gantry 20 is measured by beam angle B from an arbitrary reference position within the gantry plane 38.

A patient 42 resets on a table 46 which may be moved along a translation axis 48 aligned with the Z-axis of the Cartesian coordinate system. Table 46 crosses gantry plane 38 and is radio-translucent so as not to interfere with the imaging process.

Figure 3:
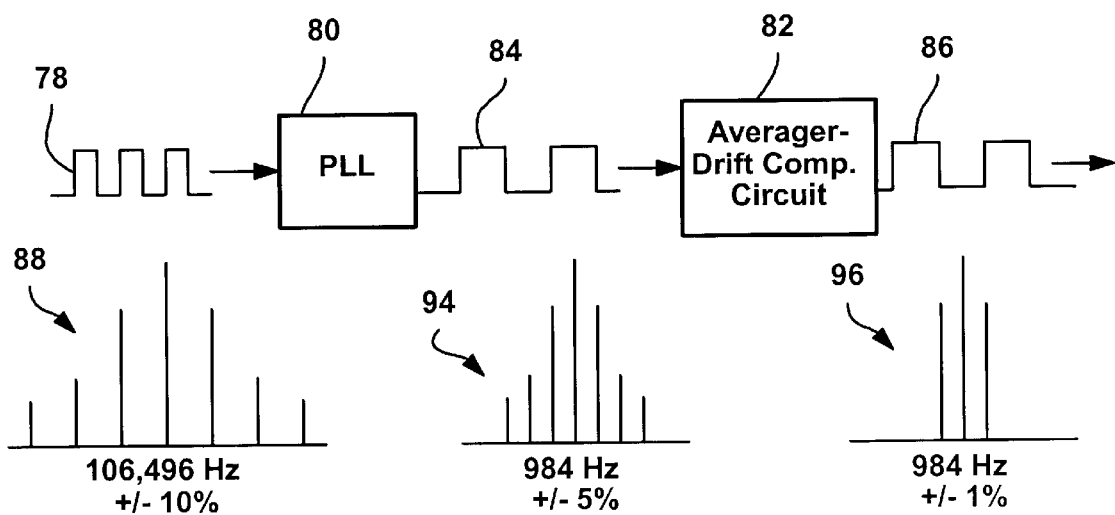
FIG. 3 is a schematic diagram illustrating processor components and exemplary system signals according to the present invention.

The x-rays of the fan beam 40 diverge from the beam axis 41 within the gantry plane 38 across a transverse axis 50 generally orthogonal to both the beam axis 41 and the translation axis 48 at a fan beam angle $\gamma$. The x-rays of beam 40 also diverge slightly from the beam axis 41 and the gantry plane 38 across the translation axis 48. Referring also to FIG. 3, a maximum beam angle $\gamma$ is identified by symbol $\Gamma$.

After passing through patient 42, the x-rays of the fan beam 40 are received by detector array 44 which has multiple columns of detector elements 18'. The detector elements 18' in exemplary array 44 are arranged in eight rows (i.e., array 44 is an eight slice detector) extending along the traverse axis 50 that subdivide array 44 along the Z-axis and a plurality of columns extending along Z or translation axis 48. The width of detector array 44 is measured along Z-axis 48. The surface of detector array 44 may be planar or may follow a section of a sphere or cylinder having a center at focal spot 26 or alternatively at the system isocenter.

The detector elements 18' each receive x-rays and provide intensity measurements along separate rays of the fan beam 40. Each intensity measurement describes the attenuation via a line integral of one fan beam ray passing through a portion of volume 43 of patient 42. The dimension of volume 43 along Z-axis 48 is greater than the Z-axis width of eight slice array 44.

Figure 2:
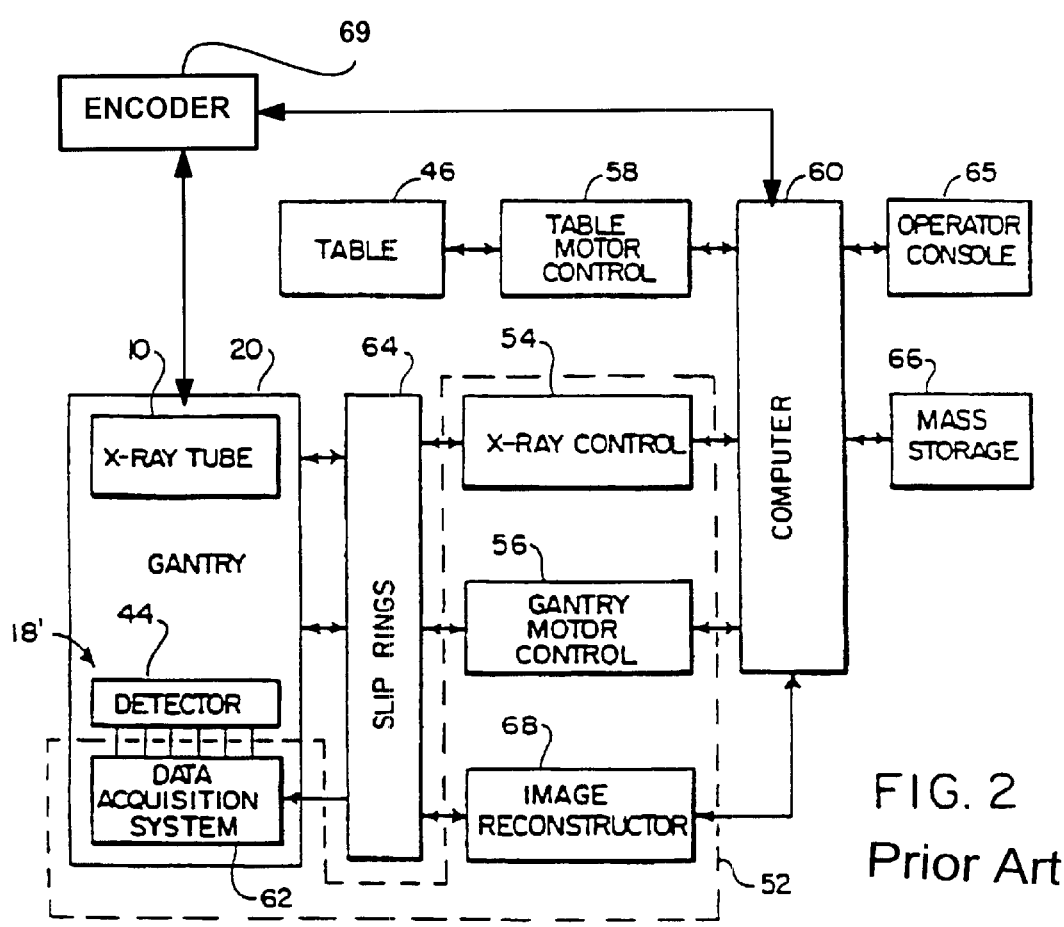
FIG. 2 is a block diagram of CT control system which may be used to control the CT apparatus of FIG. 1 and which is useful for the purposes of practicing the present invention.

Referring to FIGS. 1 and 2, an exemplary control system for controlling the CT imaging system of FIG. 1 includes gantry associated control modules collectively identified by numeral 52, a table motor control 58, slip rings 64, a central processing computer 60, an operator's console 65, a mass storage device 66 and an encoder 69. Modules 52 include an x-ray control 54, a gantry motor control 56, a data acquisition system 62 and an image reconstructor 68. X-ray control 54 provides power and timing signals to the x-ray source 10 to turn it on and off as required under the control of a computer 60. Gantry motor control 56 controls the rotational speed and position of the gantry 20 and provides information to computer 60 regarding gantry position. Data acquisition system 62 samples and digitizes intensity signals from the detector elements 18' of detector array 44 provides the digitized signals in the form of helical data row views to computer 60 for storage in mass storage device 66. Reconstructor 68 is linked to computer 60 for receiving slice image data there from and back projects the received data to, as its label implies, construct a slice image for viewing or that can be manipulated in some other manner.

Each of the above modules is connected to associated gantry mounted components via slip rings 64 and is also linked to computer 60 for control purposes Slip rings 64 permit gantry 20 to rotate continuously through angles greater than 360° to acquire projection data.

The speed and position of table 46 along translation axis 48 is controlled by computer 60 by means of table motor control 58. In addition, computer 60 runs a pulse sequencing program to perform the inventive data processing method as described in more detail below. Computer 60 receives commands and scanning parameters via operator console 65 that generally includes some type of visual interface device (e.g., a CRT display) and one or more input devices (e.g., a keyboard, a mouse controlled display cursor, etc.). Console 65 allows an operator to enter parameters for controlling a data acquiring scan and to display constructed image and other information from computer 60.

Mass storage device or memory 66 provides a means for storing operating programs for the CT imaging system, as well as image data for future reference by the operator. Both computer 60 and the image reconstructor 68 have associated electronic memory (not shown) for storing data and pulse sequencing programs.

Encoder 69 is mounted to the gantry 20 for measuring gantry and source position during data acquisition and, to that end, provides an encoder output signal that is provided to computer 60. For the purposes of this explanation it will be assumed that encoder 69 generates 106,496 separate position signals during each rotation of the gantry to identify a like number of gantry positions. In addition, unless indicated otherwise, it will be assumed that the gantry 20 is rotating at 1 Hz and therefore the encoder, over the course of each gantry rotation, averages an encoder output signal frequency of 106,496 Hz. An exemplary encoder output signal 78 is illustrated in FIG. 3 and includes a digital signal having either a high value (i.e., akin to a 1) or a low value (i.e., akin to a 0).

Figure 4:
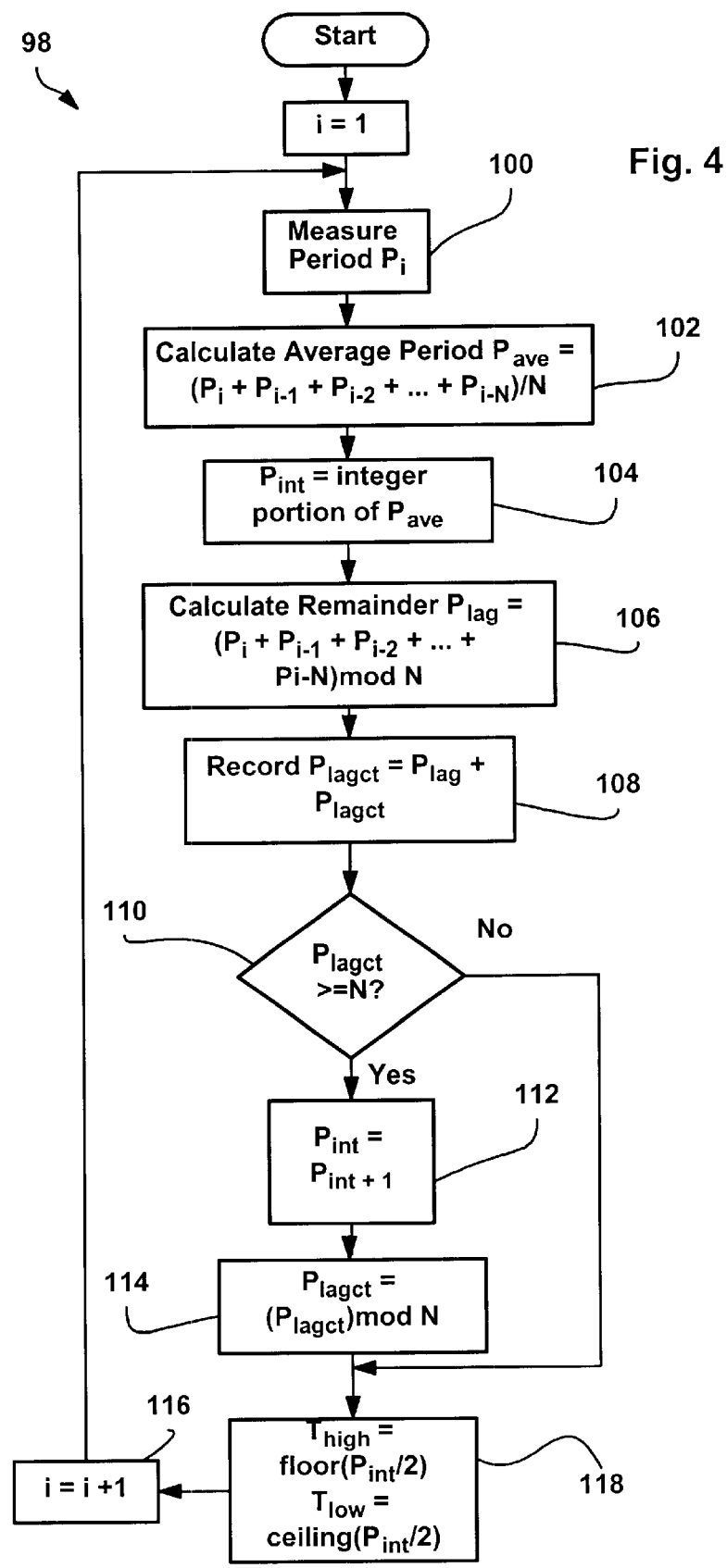
FIG. 4 is a flow chart illustrating an exemplary method according to the present invention.

As discussed above, encoder signal 78, while having a frequency of 106,496 over the course of each gantry rotation, typically has an instantaneous frequency during the course of each rotation that appreciably varies about 106,496 Hz. In FIG. 4 an exemplary encoder signal frequency spectrum 88 is shown as 106,496+/−10%.

In operation, gantry motor control 56 brings gantry 20 up to a rotational speed and table motor control 58 begins translation of table 46 along translation axis 48. The x-ray control 54 turns on x-ray source 10 and projection data is acquired on a continuous basis. The table 46 translation speed relative to the gantry rotation rate is referred to as the operating "pitch". At each gantry angle, the projection data acquired comprises intensity signals corresponding to each detector element 18' at each particular column and row of array 44. The collected data is stored in storage device 66 as helical data including row views correlated by gantry angle into separate views.

Computer 60 uses the encoder signals to identify divisions between the separate views. In the present example it will be assumed that 984 separate views are acquired during each gantry rotation. Thus, because the encoder generates 106,496 separate gantry position signals during each gantry rotation, the computer must identify a separate trigger signal every 108.23 encoder signal pulses to precisely identify the temporal boundaries between data acquired for consecutive views.

Referring still to FIG. 2 and also to FIG. 3, according to the present invention, in addition to other components, computer 60 includes a PLL 80 and an averager-drift compensator circuit 82. The PLL 80 is a conventional PLL which should be well understood by one of ordinary skill in the art and therefore is not explained here in detail. Suffice it to say that PLL 80 receives a high frequency encoder signal 78 that, in the present example, is approximately 106,496 Hz and converts that signal into a relatively low 984 Hz frequency intermediate trigger signal 84. The PLL conversion has some filtering effect on the encoder signal and therefore the PLL output trigger signal 84 will typically have less relative variance in its frequency spectrum. Thus, the exemplary intermediate trigger signal frequency spectrum in FIG. 3 is illustrated as being 984 Hz+/−5%.

The averager-drift compensating circuit 82 receives the intermediate trigger signal and performs a moving average and drift compensation process on the intermediate signal to reduce the frequency spectrum variation appreciably. To this end, it has been recognized that, while some instantaneous frequency variation occurs during each gantry rotation, because the gantry has a relatively large mass and, during acquisition, is typically characterized by a relatively large inertia, the frequency variation that occurs is typically within a relatively small frequency range and therefore the view trigger signal frequency spectrum also should remain in a small frequency range. This small frequency range limitation is particularly true over partial gantry rotations such as 5 to 10 percent of a complete rotation.

Thus, circuit 82 is programmed to, for each intermediate trigger signal cycle, identify a preceding moving average cycle period and generate a corresponding final trigger signal that essentially maintains the moving average cycle period. More specifically, circuit 82 takes the integer portion of the moving average and generates a corresponding trigger signal that follows the preceding trigger signal by a period equal to the integer portion. This process of using the integer portion to generate the trigger signal is referred to hereinafter as integer rounding.

In at least one embodiment, to make sure that the moving average reflects recent gantry rotation, the average is taken over a period corresponding to only a fraction of a complete gantry rotation. For instance, in one embodiment, the moving average may be taken over 64 intermediate trigger cycles. In this case, because 984 intermediate trigger cycles occur during each gantry rotation, the moving average corresponds to approximately 6.4% or 23 degrees of gantry rotation.

In addition, as its label implies, averager-drift compensating circuit 82 tracks drift that the integer rounding process causes and compensates for that drift. One exemplary drift compensating process is described in more detail below.

Referring now to FIG. 4, an exemplary method 98 according to the present invention is illustrated. Referring also to FIGS. 1 and 2, it should be appreciated that, when referring to FIG. 4, it is assumed that gantry 20 has already achieved a data acquiring rotational speed, in the present case, a rotational speed of 1 Hz. In addition, it is assumed that encoder 69 has already generated at least enough encoder signal pulses for a processor to perform a moving average cycle period calculation. To this end, the letter N will be used to refer to the number of cycles used to perform the moving average. For instance, where N is 64, the moving average process would include averaging signal cycles over 64 consecutive signal cycles. Herein the first intermediate signal cycle period for which the inventive process is performed will be referred to as $P_1$ meaning that the encoder 69 has provided at least N−1 signal cycles prior to period $P_1$.

Referring still to FIGS. 1, 2 and 4 and also to FIG. 3, initially the processor sets a counter i value equal to 1 at block 99. At block 100, the processor measures period $P_i$. At block 102, the processor calculates the moving average period corresponding to the N intermediate signal cycle periods including period $P_i$ and the N−1 periods that precede period $P_i$. The averaging equation can be expressed as follows:

$$P_{ave} = \frac{(P_i + P_{i-1} + P_{i-2} + \ldots + P_{i-N})}{N} \quad \text{Eq. 1}$$

At block 104, the processor identifies the integer portion $P_{int}$ of the moving average period $P_{ave}$. At block 106, the processor identifies the modulus-N of the sum period corresponding to the N periods ending with period $P_i$ as a residual or lag period $P_{lag}$. The calculation solved to identify the lag period $P_{lag}$ can be expressed as follows:

$$P_{lag} = (P_i + P_{i-1} P_{i-2} + \ldots + P_{i-N}) \bmod N \quad \text{Eq. 2}$$

Continuing, at block 108, the processor adds the lag period identified in Equation 2 to a running lag count $P_{lagct}$ thereby increasing the value of the running lag count $P_{lagct}$. This summation process can be expressed as follows:

$$P_{lagct} = P_{lagct} + P_{lag} \quad \text{Eq. 3}$$

Referring still to FIGS. 1–4, at block 110 the processor determines whether or not the lag count is equal to or greater than value N. Where the lag count is less than value N, control passes to block 118 where final trigger pulse high and low times are set according to the following two equations:

$$T_{high} = \text{floor}(P_{int}/2) \quad \text{Eq. 4}$$

$$T_{low} = \text{ceiling}(P_{int}/2) \quad \text{Eq. 5}$$

The "floor" operator corresponds to a function that rounds a corresponding value down to the nearest integer value. Similarly, the operator begins "ceiling" operator corresponds to a function that rounds a corresponding value up to the nearest integer. For examples, referring to Equation 4, if the integer portion $P_{int}$ is 9, Equation 4 would yield a $T_{high}$ value of 4 and Equation 5 would yield a $T_{low}$ value of 5. After block 118, control passes to block 116 where counter i is incremented by 1 prior to control passing back up to block 100 again where the process is repeated.

Referring again to block 110, where the lag count $P_{lagct}$ is greater than or equal the threshold value N, the cumulative drift caused by circuit 82 is at a sufficiently high value that the drift must be compensated. To this end, control passes to block 112 where the integer portion $P_{int}$ is incremented by 1. Next, at block 114 the lag count $P_{lagct}$ is set equal to the modulus-N value of the $P_{lagct}$. This calculation can be represented according to the following equation:

$$P_{lagct} = (P_{lagct}) \bmod n \quad \text{Eq. 6}$$

After block 114 process control passes to block 118 where the high and low trigger times are set according to Equations 4 and 5 above. Thereafter, control again passes to block 116 where counter i is incremented by 1. Next, as above, control passes back up to block 100 where the process is repeated for the next signal cycle.

The $T_{high}$ and $T_{low}$ values are used to generate the corrected trigger signal 86 in FIG. 3 that reflects gantry and source position more precisely and that, in the present example, would have a view frequency range of approximately 984 Hz±1%. The corrected trigger signal 86 is then used to divide acquired data into separate views as known in the art.

It should be understood that the methods and apparatuses described above are only exemplary and do not limit the scope of the invention, and that various modifications could be made by those skilled in the art that would fall under the scope of the invention. For example, the invention may be used either during data acquisition or post acquisition to divide the data into corresponding views. In addition, other averaging algorithms may be employed and, in certain cases, the N value may be larger or smaller depending upon system configuration.

To apprise the public of the scope of this invention, the following claims are made:

1. A method for use with a CT system including a gantry mounted position encoder that provides a digital encoder position signal including signal pulses that indicate gantry positions, the system including a phase locked loop (PLL) that receives the position signal and generates an intermediate trigger signal every X/Y position signals, each two consecutive intermediate trigger signals comprising a trigger pair, the method comprising the steps of:

beginning with the first trigger pair and working toward the last trigger pair in the intermediate signal, for each trigger pair:

identifying the average period corresponding to N preceding trigger pairs; and generating a final trigger signal as a function of the average period.

2. The method of claim 1 wherein the step of identifying includes the steps of:

identifying the integer portion of the average period;

identifying drift in the integer portion;

determining when the drift exceeds a threshold value; and modifying the integer portion to compensate for the drift when the drift exceeds the threshold value.

3. The method of claim 2 wherein the step of identify drift includes the steps of:

identifying a modulus-N residual corresponding to the N preceding trigger pairs as a lag value; and adding the lag value to a lag count.

4. The method of claim 3 wherein the step of determining when drift exceeds a threshold value includes the steps of determining when the lag count exceeds N.

5. The method of claim 4 wherein, when the step of modifying the integer portion includes, when the lag count exceeds N, incrementing the integer portion by one.

6. The method of claim 5 further including the step of, when the lag count exceeds N, identifying a modulus-N residual corresponding to the lag count and setting the lag count equal to the residual corresponding to the lag count.

7. The method of claim 2 wherein the trigger signal is a binary signal including a high time followed by a low time and where the step of generating the final trigger signal further includes dividing the integer portion by two to generate a half period, rounding the half period up and down to generate ceiling and floor periods, respectively, setting a one of the low and high times equal to one of the floor and ceiling periods and setting the other of the low and high times equal to the other of the floor and ceiling periods.

8. The method of claim 7 wherein the steps of setting the low and high times includes setting the high time equal to the floor period and setting the low time equal to the ceiling period.

9. The method of claim 1 wherein N includes the N immediately preceding pulse pairs.

10. The method of claim 1 wherein N corresponds to a fraction of a complete gantry rotation.

11. The method of claim 10 wherein N corresponds to 3 to 50 percent of a complete gantry rotation.

12. A method for use with a CT system including a gantry mounted position encoder that provides a digital encoder position signal including signal pulses that indicate gantry positions, the system including a phase locked loop (PLL) that receives the position signal and generates an intermediate trigger signal every X/Y position signals, each two consecutive intermediate trigger signals comprising a trigger pair, the method comprising the steps of:

beginning with the first trigger pair and working toward the last trigger pair in the intermediate signal, for each trigger pair:

identifying the integer portion of an average period corresponding to N preceding trigger pairs;

identifying a modulus-N residual corresponding to the N preceding trigger pairs as a lag value;

adding the lag value to a lag count;

determining when the lag count exceeds N and, where the lag count exceeds N:

(i) incrementing the integer portion by one;

(ii) identifying a modulus-N residual corresponding to the lag count;

(iii) setting the lag count equal to the residual corresponding to the lag count; and generating a final binary trigger signal including a high time followed by a low time, the step of generating including, dividing the integer portion by two to generate a half period, rounding the half period up and down to generate ceiling and floor periods, respectively, setting one of the low and high times equal to one of the floor and ceiling periods and setting the other of the low and high times equal to the other of the floor and ceiling periods.

13. An apparatus for use with a CT system including a gantry mounted position encoder that provides a digital encoder position signal including signal pulses that indicate gantry positions, the system including a phase locked loop (PLL) that receives the position signal and generates an intermediate trigger signal every X/Y position signals, each two consecutive intermediate trigger signals comprising a trigger pair, the apparatus comprising:

a program running a pulse sequencing program to perform the steps of:

beginning with the first trigger pair and working toward the last trigger pair in the intermediate signal, for each trigger pair:

identifying an average period corresponding to N preceding trigger pairs; and generating a final trigger signal as a function of the average period.

14. The apparatus of claim 13 wherein the program causes the processor to perform the step of generating by performing the steps of:

identifying the integer portion of the average period identifying a modulus-N residual corresponding to the N preceding trigger pairs as a lag value;

adding the lag value to a lag count;

determining when the lag count exceeds N and, where the lag count exceeds N:

(i) incrementing the integer portion by one;

(ii) identifying a modulus-N residual corresponding to the lag count;

(iii) setting the lag count equal to the residual corresponding to the lag count; and generating a final binary trigger signal corresponding to the integer portion.

15. The apparatus of claim 14 wherein the final trigger signal includes a high time followed by a low time and wherein the program causes the processor to perform the step of generating by dividing the integer portion by two to generate a half period, rounding the half period up and down to generate ceiling and floor periods, respectively, setting one of the low and high times equal to one of the floor and ceiling periods and setting the other of the low and high times equal to the other of the floor and ceiling periods.

16. The apparatus of claim 15 wherein the program causes the processor to perform the steps of setting the low and high times by setting the high time equal to the floor period and setting the low time equal to the ceiling period.

17. The apparatus of claim 14 wherein N includes the N immediately preceding pulse pairs.

18. The apparatus of claim 14 wherein N corresponds to a fraction of a complete gantry rotation.

19. The apparatus of claim 18 wherein N corresponds to 3 to 50 percent of a complete gantry rotation.

\* \* \* \* \*